(12) United States Patent
Zhang et al.

(10) Patent No.: US 9,486,434 B2
(45) Date of Patent: Nov. 8, 2016

(54) METHOD FOR DELIVERY AND USE OF ISOTHIOCYANATES FOR PROPHYLAXIS AND/OR THERAPY OF BLADDER CANCER

(75) Inventors: Yuesheng Zhang, Orchard Park, NY (US); Arup Bhattacharya, Buffalo, NY (US); Li Tang, Lancaster, NY (US); Yun Li, Orchard Park, NY (US); Joseph D. Paonessa, Niagara Falls, NY (US); Feng Geng, Columbus, OH (US); Yi Ding, Buffalo, NY (US)

(73) Assignee: Health Research Inc., Buffalo, NY (US)

( * ) Notice: Subject to any disclaimer, the term of this patent is extended or adjusted under 35 U.S.C. 154(b) by 227 days.

(21) Appl. No.: 13/609,531

(22) Filed: Sep. 11, 2012

(65) Prior Publication Data

US 2013/0072554 A1  Mar. 21, 2013

Related U.S. Application Data

(63) Continuation-in-part of application No. PCT/US2011/028076, filed on Mar. 11, 2011.

(60) Provisional application No. 61/313,004, filed on Mar. 11, 2010.

(51) Int. Cl.
   *A61K 36/31* (2006.01)
   *A61K 31/26* (2006.01)

(52) U.S. Cl.
   CPC .............. *A61K 31/26* (2013.01); *A61K 36/31* (2013.01); *A61K 2236/10* (2013.01)

(58) Field of Classification Search
   None
   See application file for complete search history.

(56) References Cited

U.S. PATENT DOCUMENTS

| | | | |
|---|---|---|---|
| 5,968,505 A | 10/1999 | Fahey et al. | |
| 6,436,450 B1 | 8/2002 | Omary et al. | |
| 7,402,569 B2 | 7/2008 | Fahey | |
| 2002/0061352 A1 | 5/2002 | Ekanayake et al. | |
| 2002/0147155 A1 | 10/2002 | Foster et al. | |
| 2006/0127996 A1* | 6/2006 | Fahey | 435/128 |
| 2008/0044497 A1 | 2/2008 | Sussan et al. | |
| 2008/0311276 A1 | 12/2008 | West et al. | |
| 2009/0286961 A1* | 11/2009 | Tang | 530/378 |

FOREIGN PATENT DOCUMENTS

| | | |
|---|---|---|
| CA | 2728492 | 1/2010 |
| CN | 101229211 A | 7/2008 |
| CN | 101328197 A | 12/2008 |

OTHER PUBLICATIONS

Matusheki, Nathan V. et al. Heating decreases epithiospecifier protein activity and increases sulforaphane formation in broccoli, Phytochemistry, May 31, 2004, vol. 65(9), pp. 1273-1281.

Zhang et al., The Biolochical Activities of the Hydrolytes (Isothiocyanates) of Glucosinolates in Horseradish and Cruciferous Vegetables, Food Research and Development, 2005 26(3), 83-88. Jun. 30, 2005.

Bhattacharya Arup et al., Database Biosis [Online], Biosciences Information Service, "Allyl isothiocyanate-rich mustard seed powder inhibits bladder cancer growth and muscle invasion", Dec. 2010, vol. 31, No. 12, pp. 2105-2110.

* cited by examiner

*Primary Examiner* — Terry A McKelvey
*Assistant Examiner* — Catheryne Chen
(74) *Attorney, Agent, or Firm* — Hodgson Russ LLP

(57) ABSTRACT

Provided is a composition that contains a mixture of broccoli seed and mustard seed. Before mixing the broccoli seed with the mustard seed, the broccoli seed is subjected to baking and a pressurized heat treatment. The broccoli seed is baked at a temperature of at least 200 degrees Fahrenheit for at least 60 minutes, and is subjected to a pressurized heat treatment of at least 200 degrees Fahrenheit at a pressure of at least 10 pounds/square inch for at least 5 minutes. Also provided is a method for therapy and/or prophylaxis of bladder cancer in an individual. The method entails administering orally to the individual a composition that contains an isothiocyanate (ITC) or a derivative thereof such that the administration inhibits the growth and/or recurrence of bladder cancer. Nutraceutical compositions are also provided.

6 Claims, 13 Drawing Sheets

US 9,486,434 B2

METHOD FOR DELIVERY AND USE OF ISOTHIOCYANATES FOR PROPHYLAXIS AND/OR THERAPY OF BLADDER CANCER

CROSS-REFERENCE TO RELATED APPLICATIONS

This application is a continuation-in-part application of International Application PCT/US2011/028076, with an international filing date of Mar. 11, 2011, which claims priority to U.S. Provisional Patent Application No. 61/313,004, filed Mar. 11, 2010, the disclosures of each of which are incorporated herein by reference.

GOVERNMENT RIGHTS

This invention was made with government support under R01 CA124627 awarded by the National Cancer Institute. The government has certain rights in the invention.

FIELD OF THE INVENTION

The present invention relates generally to the field of cancer therapy and more specifically to the use of isothiocyanates (ITCs) for therapy and/or prophylaxis of bladder cancer

BACKGROUND OF THE INVENTION

Bladder cancer is the fourth and eighth most common malignancy in men and women respectively in the Western world [1], with the majority (~80%) being initially diagnosed as a superficial non-invasive cancer for which transurethral resection remains the first choice of treatment, followed by intravesical immuno- or chemo-therapy in cases with high risk of recurrence. Despite this, almost 80% of patients will develop recurrence with ~10% progressing to more aggressive muscle-invasive carcinoma [2, 3]. Patients who present with higher stages of the disease progress even more frequently and a third of them die due to the disease. The median age of bladder cancer diagnosis is in the late 60s [4]. Cisplatin-based combination chemotherapy remains the mainstay therapy for invasive bladder cancers. Renal dysfunction and poor performance status often seen at this advanced age preclude cisplatin chemotherapy and other regimes used are considered suboptimal compared to cisplatin-based therapy [5]. Cystectomy and chemo- and radiation-therapy are often associated with significant morbidity and mortality [4]. Consequently, bladder cancer remains as one of the most expensive cancers to treat and manage. Furthermore, the majority of human bladder cancers are detected as superficial cancer without muscle invasion and are treated with transurethral resection. Thus, patients who are at high risk of recurrence are treated after the surgery by immunotherapy with attenuated *Bacillus* Calmettes-Guerin (BCG) or chemotherapy such as mitomycin, to inhibit recurrence. These therapies not only mandate transurethral delivery in order to prevent systemic toxic effects, but also have limited efficacy and significant local adverse effects. On the other hand, a significant percentage of patients who present with muscle invasive bladder cancer have no prior incidence of the superficial disease, and ~50% of patients with invasive bladder cancer already have distant metastases at the time of presentation [6]. Despite a high initial response rate of 40-70% in metastatic disease, the overall survival is only 5-20% with chemotherapy [5]. Thus, there is an ongoing and unmet need for methods for bladder cancer therapy and prophylaxis, particularly for the recurring bladder cancer.

SUMMARY OF THE INVENTION

The present invention provides compositions and methods for therapy and/or prophylaxis of bladder cancer. The method comprises administering to an individual diagnosed with, suspected of having, or at risk for developing bladder cancer a composition comprising one or more ITCs, such that the administration of the ITC inhibits the growth, muscle invasion and/or recurrence of bladder cancer. The compositions comprise various ITCs, including but not limited to various mixtures of vegetable products that contain ITCs or their precursors (glucosinolates).

In one embodiment, the invention includes a method comprising administering a composition comprising ITCs, wherein the ITC is provided as an ITC-containing vegetable product. The vegetable products include but are not limited to broccoli/broccoli sprout extract, broccoli seed powder, mustard seed powder, horseradish meal/powder, wasabi powder or combinations thereof. In one embodiment, the vegetable product comprises broccoli seeds. The seeds are prepared for use in treatment and/or prophylaxis of bladder cancer by being subjected to baking and a pressurized heat treatment, such as autoclaving. We have discovered that this process inactivates epithiospecifier protein (ESP), which is beneficial when the seeds treated accordingly are combined with sinigrin-containing products, such as mustard seed powder. Thus, in one embodiment, the broccoli product used in the present invention comprises heat/pressure inactivated ESP. This unique procedure yields a stable product that is suitable for optimized delivery of both allyl isothiocyanate (AITC) and sulforaphane (SF).

The invention also provides a unique dosing regime whereby a composition comprising at least one ITC is administered to an individual orally and preferably near the time when the individual is about to fall asleep. The dosing regime comprises administering a single or multiple non toxic dose of the ITC to the individual daily for a period of at least several days.

In various embodiments, the ITC is an isolated and/or purified/or synthetic ITC that is provided as a pharmaceutical preparation. Some examples of ITCs are AITC, benzyl isothiocyanate (BITC), phenethyl isothiocyanate (PEITC) and SF. In another embodiment, the derivatives and/or metabolites of ITCs which include the glutathione conjugates, cystinylglycine conjugates, cysteine conjugates and N-acetylcysteine (NAC) conjugates are administered either singly or in various combinations.

In addition the foregoing, the present invention provides a nutraceutical and method for using it to improve the well-being of an individual who has or as at risk for developing bladder cancer.

DESCRIPTION OF THE INVENTION

Figure 1:
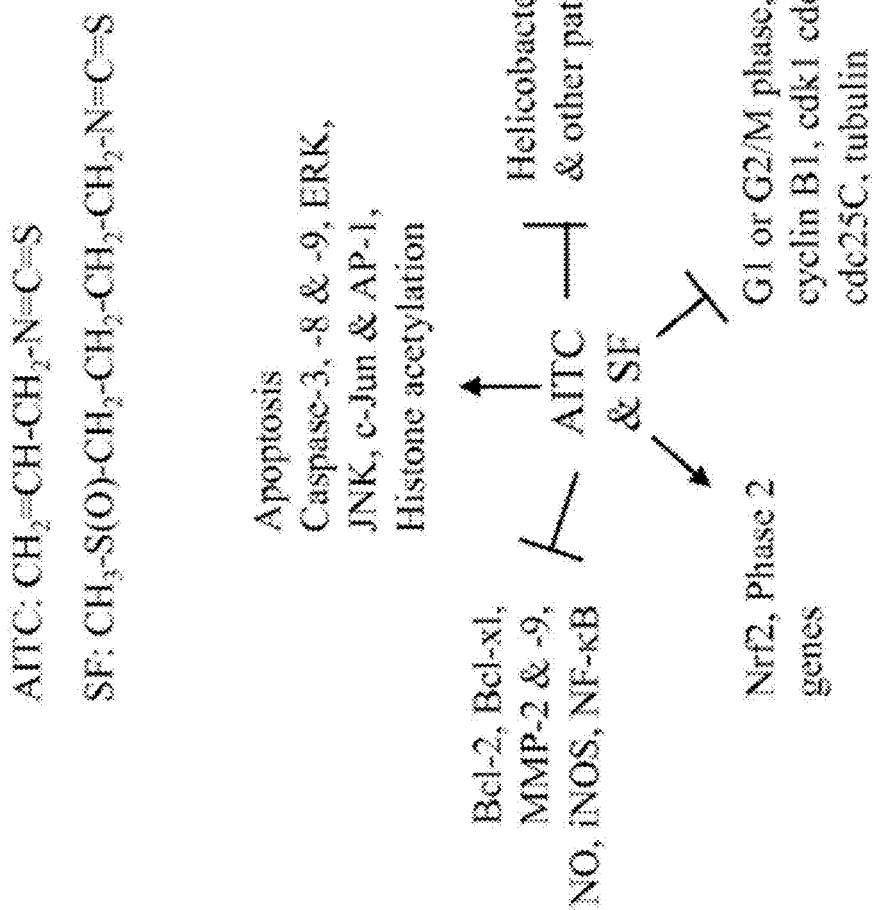
FIG. 1. Chemical structures and putative anticancer mechanisms of AITC and SF. The arrows indicate activation, and the T symbols indicate inhibition. The information is compiled from a collection of published studies in different cell lines.
Figure 2:
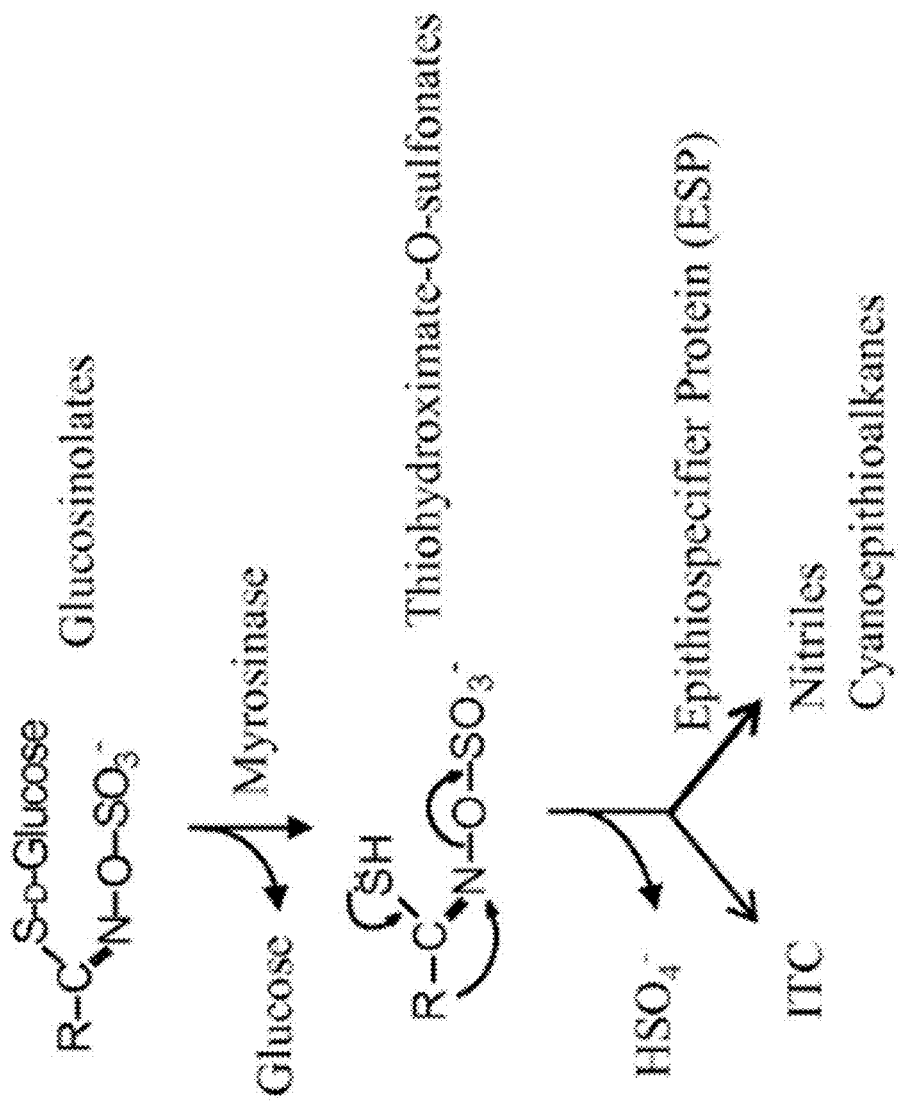
FIG. 2. Myrosinase catalyzed conversion of glucosinolates to ITC and its interference by ESP.

The present invention is related to the use of compositions comprising ITCs for therapy and/or prophylaxis of bladder cancer. ITCs occur in commonly consumed cruciferous vegetables. For example, AITC (see FIG. 1 for its chemical structure) is abundant in mustard, horseradish and wasabi [8], and SF is abundant in broccoli (See FIG. 1 for its chemical structure) ITCs are stored as biologically inert glucosinolates (β-thioglucoside N-hydroxysulfates) in cruciferous vegetables, and the glucosinolates such as sinigrin (AITC glucosinolate) and glucuroraphanin (SF glucosinolate) are converted by enzyme myrosinase (a thioglucoside glucohydrolase) to thiohydroximate-O-sulfonates, which rapidly and spontaneously rearrange to give rise to the ITCs. Myrosinase is often present in the same plants but are separated from the glucosinolates under normal conditions. However, some plants also possess ESP, which converts thiohydroximate-O-sulfonates to biologically-insignificant nitriles and cyanoepithioalkanes at the expense of ITCs (FIG. 2). ESP is known to exist in broccoli and broccoli seed [7], but not in mustard seed. It is also known that some conversion to ITCs of ingested glucosinolates that escape plant myrosinase may occur in vivo via the myrosinase activity of intestinal microbial flora in humans and animals [11]. AITC and SF as well as other ITCs are considered to have very high bioavailabilty and are primarily eliminated through urinary excretion [12-14]. ITCs are metabolized primarily through the mercapturic acid pathway in vivo resulting in the formation of N-acetylcysteine (NAC) conjugates that are excreted through urine. The NAC conjugates themselves are not biologically active, but they dissociate to the parent ITCs when stored in the urine in the bladder, thus acting as prodrugs of ITCs. In various embodiments, the compositions and methods of the invention include providing an ITC with a thiol conjugate or a derivative thereof. In one embodiment, a derivative of the thiol conjugate is an N-acetylcysteine conjugate.

AITC and SF [11, 15] as well as other ITCs have been shown to have antimicrobial and insecticidal activity. Chemopreventive activities of these compounds may also be due in part to their ability to inhibit phase I enzymes and induce phase II enzymes [14]. Putative chemopreventive mechanisms of AITC and SF are summarized in FIG. 1. However, the art is devoid of any recognition or demonstration that ITCs can be used in methods designed for prophylaxis or therapy of bladder cancer, and there is no teaching in the art of ITC formulations that would be suitable for prophylaxis and/or therapy of bladder cancer. Moreover, the art is also devoid of any suggestion of subjecting a broccoli product, such as broccoli seeds, to baking and pressurized heat, such as pressurized heat in the form of pressurized steam treatments (i.e., autoclaving). Thus, it is believed this is the first disclosure of a method for treating a broccoli product with baking and a pressurized heat treatment, and combing such a treated broccoli product with a mustard product to provide a composition that has therapeutic and/or prophylactic utility for use against bladder cancer. Without intending to be bound by any particular theory, it is also considered that the method for treating a broccoli product disclosed herein functions to destroy its endogenous ESP. Thus, when the treated broccoli product is mixed with a suitable mustard product, such as mustard seed powder, it provides for a stable, optimized composition that can be used for delivery of both AITC and SF.

Figure 5:
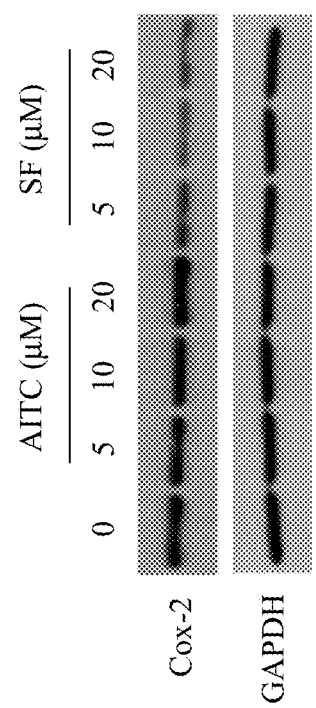
FIG. 5. The effects of AITC and SF on cyclooxygenase-2 (Cox-2) expression in human bladder cancer cells. Human bladder cancer HT1376 cells that over express Cox-2 were treated with AITC or SF at the indicated concentrations for 24 h and then harvested for Western blot analysis of Cox-2. GAPDH is used as a loading control.

In more detail, the present invention is based on our surprising discoveries that certain ITCs, such as AITC, SF, and ITC-containing vegetable products such as mustard seed powder and a mixture of mustard seed powder and broccoli seed powder are suitable for therapy and/or prophylaxis of bladder cancer when delivered orally. In particular, we demonstrate that AITC causes strong cell cycle arrest (mitotic arrest) and apoptosis (mitotic catastrophe) in bladder cancer cells but is markedly less toxic to normal human bladder epithelial cells. The compositions and method of the invention are demonstrated to inhibit cancer development, including inhibition of muscle invasion in the bladder at a very low dose level, and to be selectively delivered to the bladder cancer tissue through urinary excretion. Thus, it is considered that a mixture of AITC-rich mustard seed powder and heat-treated broccoli seed powder will be suitable for use in human bladder cancer therapy. In this regard, SF strongly down regulates cyclooxygenase-2 (Cox-2), which is a well-known target against bladder cancer, whereas AITC does not show such activity (FIG. 5). Further, particular embodiments of the method are demonstrated in an orthotopic rat bladder cancer model. Thus, the method of the invention is shown to function in vivo.

In various embodiments, the present invention provides a composition comprising a mixture of a vegetable product and a mustard product, wherein the vegetable product has been subjected to baking and a pressurized heat treatment, which may be provided as a pressurized steam treatment.

Vegetable products suitable for use in the invention include but are not limited to broccoli/broccoli sprout extract, broccoli seed powder, mustard seed powder, horseradish meal/powder, wasabi powder or combinations thereof. In certain embodiments, the vegetable product is any cruciferous vegetable or a product derived therefrom.

In various embodiments, the cruciferous vegetable product is a composition comprising or consisting essentially of or consisting of a broccoli product. In certain embodiments, the broccoli product comprises or consists essentially of or consists of broccoli seed.

In various embodiments, the cruciferous vegetable product is used in combination with a mustard product. The mustard product can comprise or consist essentially of or consist of mustard seed.

In certain embodiments, a composition of the invention comprises or consists essentially of or consists of a mixture of broccoli seed and mustard seed. The broccoli seed and/or the mustard seed may be provided in a powder form.

In one embodiment, the broccoli product, such as broccoli seed, which can be provided as a broccoli seed powder, is baked at a temperature and for a period of time sufficient to inactive some or all epithiospecifier protein (ESP) in the broccoli product. Those skilled in the art will recognize how to determine whether ESP has been inactivated. For instance, ESP inactivation can be determined as described by Matusheski et al [7], which methods are incorporated herein by reference.

In various embodiments, the broccoli product is baked at least 200 degrees Fahrenheit (F) for at least 30 minutes. The baking may be performed for any period of time from 10 minutes to 300 minutes, inclusive, and including all digits there between, and all numbers between consecutive integers to the tenth decimal point. In one embodiment, broccoli product is baked at 250 degrees F. for at least 90 minutes.

The broccoli product can also be subjected to a pressurized heat treatment. The pressurized heat treatment can comprise a pressurized steam treatment, i.e., the pressurized heat treatment can comprise autoclaving. In various embodiments, the pressurized heat treatment is carried out at least 200 degrees F. for at least five minutes at a pressure of at least 10 pounds/square inch (p.s.i.).

It will be recognized from the foregoing that the baking and/or the pressurized heat treatment, which may be a pressurized steam treatment, can be performed using a temperature of at least 200 degrees, and can be performed at any temperature from 200 degrees to 350 degrees F., inclusive, and including all digits there between, and all numbers between consecutive integers to the tenth decimal point. The pressurized heat treatment, which can be a pressurized steam treatment such as autoclaving, can be carried out at a pressure of at least 10 pounds/square inch (p.s.i.), and up to a pressure of 40 p.s.i., inclusive, and including all digits there between, and all numbers between consecutive integers to the tenth decimal point. In one embodiment, the pressurized steam treatment is performed at 15 p.s.i. In one embodiment, the broccoli product is subjected to a pressurized steam treatment at 15 p.s.i. for 15 minutes, and at any temperature disclosed herein. It will be recognized that, if desired, the temperature and/or pressure used to treat the broccoli product can be varied during the course of one or multiple treatments.

The baking and pressurized steam treatment are preferably performed by consecutively baking and performing the pressurized steam treatment, in that order. In one embodiment, the mustard product and broccoli product are not mixed until the broccoli product has been subjected to a baking and pressurized heat treatment. In one embodiment, the composition comprising a mixture of broccoli product that has been baked and subjected to a pressurized heat treatment comprises a mustard product that has not been baked or subjected to a pressurized heat treatment. Thus, in one embodiment, a composition that comprises a mixture of the treated broccoli product and the mustard product contains no mustard product that has been baked and/or no mustard product that has been subjected to a pressurized heat product.

The broccoli and mustard products may be mixed in any ratio. In particular embodiments, they can be mixed in from a 1:1 to 10:1 ratio, inclusive, and including all digits there between, and all numbers between consecutive integers to the tenth decimal point. The described ratios can be broccoli product to mustard product, and vice versa. All ratios that can maximize hydrolysis of glucosinolates are contemplated by the invention.

The broccoli product and/or the mustard product can be ground into a powder before or after the broccoli powder is treated by baking, and/or before or after the broccoli product is subjected to a pressurized heat treatment. In various embodiments, the powders can comprise broccoli and/or mustard particles that are less than 1 mm in diameter. In various embodiments, a powder of the invention can comprise at least 50%, 60%, 70%, 80%, 90%, 99%, or 100% particles that are less than 1 mm in diameter. In certain embodiments, the particle sizes can be as small as 5 microns in diameter.

Without intending to be bound by theory, it is considered that the treated broccoli/mustard seed powder mixture provided by the invention comprises a stable source of both AITC and SF, since they are stored as glucosinolates (sinigrin and glucoraphanin), and provides an optimal amount of AITC and SF upon hydration or ingestion, since the myrosinase in the mustard seed powder will hydrolyze the glucosinolates without interference by ESP.

In various embodiments, the cruciferous vegetable product comprises glucoraphanin-rich broccoli seeds. In particular embodiments, the glucoraphanin-rich broccoli seeds comprise at least 50, 60, 70, 80, 90 or 100, or 110 micromoles/gram, including all integers there between, and all numbers between consecutive integers to the tenth decimal point, of glucoraphanin.

In various embodiments, the mustard product comprises at least 50, 60, 70, 80, 90 or 100, or 110 micromoles/gram, including all integers there between, and all numbers between consecutive integers to the tenth decimal point, of sinigrin. Such cruciferous vegetable and mustard products can be present in the compositions of the inventions, and can be used in the method of the invention.

Those skilled in the art will recognize that the invention encompasses methods of making the compositions of the invention. The methods of making the compositions of the invention include but are not necessarily limited to performing any or all of the above described processes and using any or all of the aforementioned temperatures, pressures, time parameters, and broccoli and mustard products with any or all of the functional and/or physical properties described above. Thus, in one embodiment, the method of making a composition of the invention comprises subjecting a broccoli product to baking and a pressurized heat treatment as described herein, and then combining the broccoli product with a mustard product.

The method of the invention for prophylaxis and/or therapy of bladder cancer comprises in one embodiment oral delivery of a composition comprising an ITC or ITCs or their precursors or NAC-AITC conjugates to an individual in need thereof such that the ITCs are selectively delivered to the bladder, through urinary excretion, to specifically inhibit bladder cancer growth/recurrence and/or metastasis, such as the spread of the disease through muscle invasion.

In one embodiment, the ITC is administered to an individual as a composition comprising isolated and/or purified ITC and/or synthetic ITC. The ITC can be any suitable ITC. The composition may comprise, consist essentially of, or consist of an ITC. For example, the composition may comprise between 10%-100%, including all digits there between, of an ITC or a combination of more than one ITC. In one embodiment, the composition comprises mustard seed powder. In one embodiment, the composition comprises mustard seed powder and broccoli seed powder, the latter of which is prepared from heat-treated seeds (i.e, baking and autoclaving as described above).

The composition comprising an ITC such as AITC or its derivatives including but not limited to NAC conjugates can be formulated for oral delivery in any suitable form and/or delivery vehicle. For instance, the composition can be provided as a powder, liquid, gel, spray, suspension, emulsion, a tablet, capsule, as an extended or rapid release formulation, etc. The compositions may be provided as an aqueous solution, which can further comprise suitably flavored syrups, aqueous or oil suspensions, or flavored emulsions with edible oils. The oral delivery method can include without limitation swallowing or delivery to the stomach by, for example, a medical device such as a feeding tube. The composition may also be delivered directly to the bladder if desired by, for example, catheterization.

Compositions used in the method of the invention may comprise pharmaceutically acceptable carriers, excipients and/or stabilizers. Some examples of compositions suitable for mixing with the ITC can be found in: *Remington: The Science and Practice of Pharmacy* (2005) 21st Edition, Philadelphia, Pa. Lippincott Williams & Wilkins.

In one embodiment, the method of the invention is performed for a person in need of bladder cancer therapy or of prophylaxis of bladder cancer. Thus, the individual to whom the composition comprising the ITC is administered can be an individual who is at risk for, or is suspected of having, or has been diagnosed with bladder cancer. The individual may also be at risk for recurrent bladder cancer, and/or metastasis of bladder cancer. In one embodiment, the individual is an individual who has previously been treated for bladder cancer.

The method of the invention can be performed in conjunction with conventional therapies that are intended to treat or prevent bladder cancer. For example, additional treatment modalities including but not limited to chemotherapies, surgical interventions, and radiation therapy that can be performed prior to, concurrently, or subsequent to the method of the invention.

The present invention also provides a novel dosing regime for therapy and/or prophylaxis of bladder cancer. Our results are surprising in that, contrary to conventional belief that in general the benefits of consumption of cruciferous vegetables and/or extracts thereof increase with the volume consumed, we demonstrate that higher doses of ITCs are not better than certain lower doses at inhibiting the growth and muscle invasion of bladder cancer. Further, we demonstrate that not all natural products that contain ITC precursors (glucosinolates), necessarily inhibit bladder cancer growth. For instance, we demonstrate that sinigrin, the precursor of AITC, has no anticancer activity itself and is minimally hydrolyzed in vivo by myrosinase of intestinal microflora. Accordingly, in one embodiment, a novel dosing regime of the invention comprises oral administration of a composition comprising AITC, wherein the AITC is provided to the individual at a non toxic dosage. Specific but non-limiting examples of dosages include but not limited to 5, 10, 25 and 50 micromols/kg, inclusive, and including all digits there between, and all numbers between consecutive integers to the tenth decimal point.

Administration of the composition comprising the ITC can be performed at any time. It is preferable to administer the composition near the time the individual falls asleep so that the ITC can be concentrated in the urine in the bladder of the individual. Thus, in one embodiment, the administration is performed at night. Without intending to be bound by any particular theory, it is considered that this provides an increased localized concentration in the bladder of the individual that is effective to inhibit the growth of bladder cancer cells/tumors. The composition comprising the ITC can also be administered at other times of the day. The administrations can be repeated once daily, or more than once daily, and the administrations can be continued for any desired period, such as for several days, weeks, months or years.

The efficacy of the method of the invention can be evidenced by a variety of parameters which include but are not limited to inhibition of the growth of bladder cancer cells and/or bladder tumor(s), inhibition of bladder cancer invasion and metastasis, and/or prolongation of the survival of an individual who has bladder cancer.

In addition the foregoing, in one embodiment, the present invention provides a nutraceutical and method for using it to improve the well-being of an individual who has or as at risk for bladder cancer. "Nutraceutical" is a term coined by combining "nutritional" and "pharmaceutical." It is generally used to identify foods and/or supplements and/or food components that are believed to have a beneficial effect on health or other aspects of well-being. Nutraceuticals are often used in the health food and supplement industry, while medications, which are designed to treat, cure, and/or prevent disease, are subject to different regulatory provisions and agencies than nutraceuticals, even though some nutraceuticals can be effective for the same purposes as those for which medications are used. Nutraceuticals can comprise an active substance, and they are frequently used at a certain time or with a certain time pattern and in a manner that keeps the concentration of nutraceutical and/or its active substance at a certain value to achieve a desired. In this regard, in some embodiments, the composition of the invention which comprises a mixture of broccoli seed and mustard seed, wherein the broccoli seed has been subjected to baking and a pressurized heat treatment before being mixed with the mustard seed, can be considered a nutraceutical. Likewise, the glucoraphanin and sinigrin can be considered active substances comprised by the nutraceutical. Additionally, N-acetylcysteine (NAC) conjugates can be considered to be an active substance comprised by the nutraceutical. Composition comprising the active ingredients can be prepared according to the foregoing description of the compositions and methods for making them.

In one embodiment, the invention provides a method for delivering an active substance to a human comprising the step of administering to the individual a composition comprising a mixture of broccoli seed and mustard seed, wherein the broccoli seed has been subjected to baking and a pressurized heat treatment before being mixed with the mustard seed, and wherein the active substance in the composition is glucoraphanin, sinigrin, other glucosinolates, an ITC, a NAC-ITC conjugate, or a combination thereof. This method can be performed according to the foregoing description of methods for delivering compositions of the invention.

The following examples are intended to illustrate but not limit the invention.

Example 1

Figure 3:
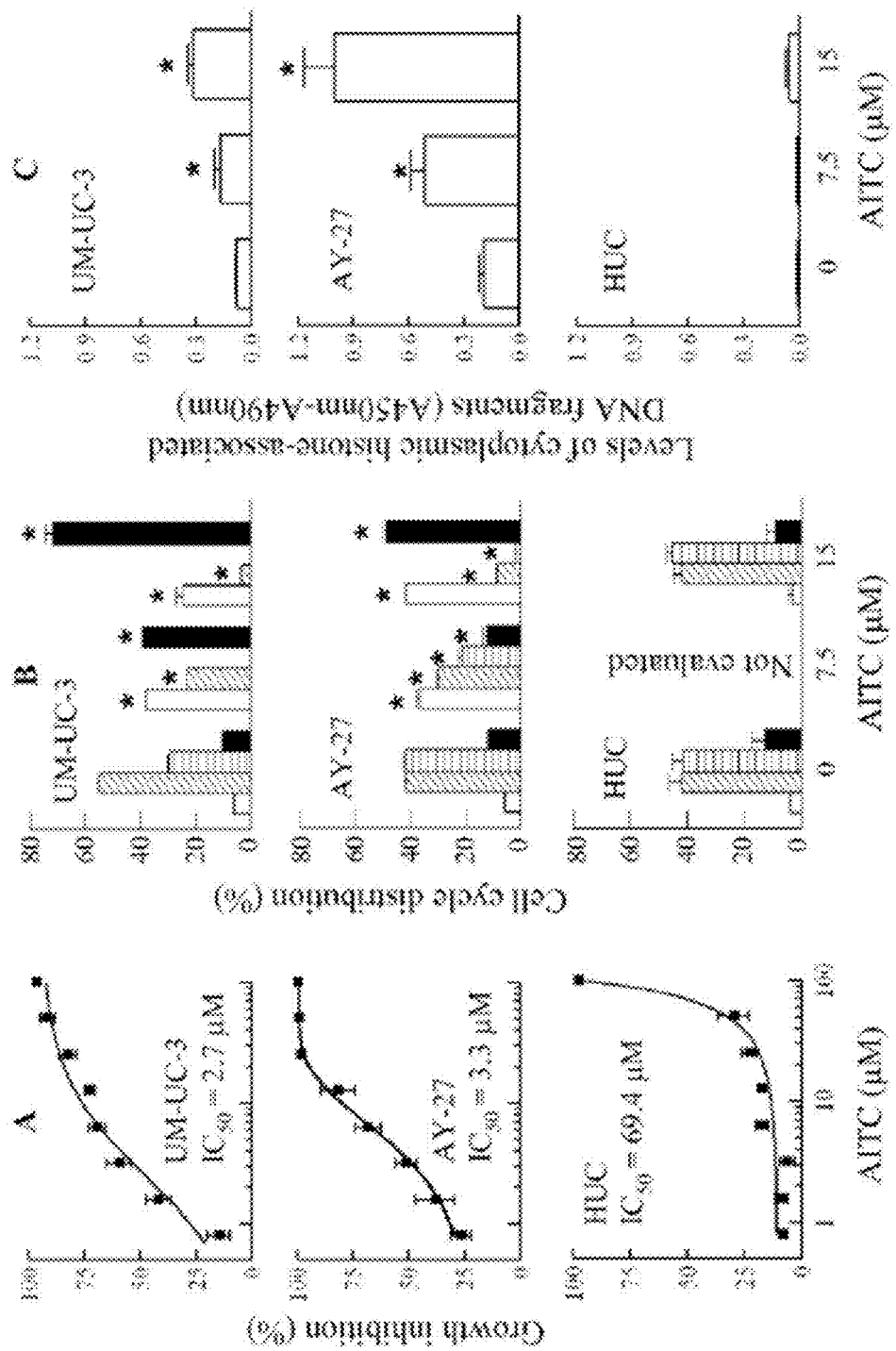
FIG. 3. The effect of AITC on cell survival and proliferation. AITC was evaluated at the indicated concentrations in human bladder cancer UM-UC-3 cells, rat bladder cancer AY-27 cells, and normal human bladder epithelial cells (HUC). A. Cell growth inhibition, measured by MTT assay, 72-h AITC treatment. $IC_{50}$ was calculated from nonlinear regression curve fit. B. Cell cycle arrest (□, subG1; ▨, G1; ▤, 5; ■, G2/M), measured by flow cytometry, 24 h AITC treatment. C. Apoptosis induction, measured by an ELISA assay, 24 h AITC treatment. Mean±SE, n=3-6), *P<0.05.

This Example demonstrates the effect of AITC on proliferation and survival of normal and malignant bladder cancer cells. Treatment with AITC of human bladder carcinoma UM-UC-3 cells and rat bladder carcinoma AY-27 cells led to a dose-dependent inhibition of cell proliferation with an $IC_{50}$ of 2.7 and 3.3 microM, respectively (FIG. 3A). This inhibition was associated with profound cell cycle arrest with up to 72% of UM-UC-3 cells and 49% of AY-27 cells in G2/M phase after treatment with AITC at 7.5-15 microM for 24 h, compared to 9.9-11.5% of control cells that were in G2/M phase (FIG. 3B). Strong apoptosis induction by AITC was also seen as indicated by up to 6.5 fold (UM-UC-3) and 7.8 fold (AY-27) increases in subG1 population (FIG. 3B), and up to 3.9 fold (UM-UC-3) and 5.2 fold (AY-27) increases in cytoplasmic levels of histone-associated DNA (FIG. 3C). In contrast, AITC was found to be much less toxic to normal human bladder epithelial cells (HUC) with an $IC_{50}$ of 69.4 microM (FIG. 3A), which was 21.0-25.7 times higher than the corresponding $IC_{50}$ of AITC in their malignant counterparts. Further, AITC at 7.5 and/or 15 microM failed to cause cell cycle arrest and apoptosis in HUC (FIGS. 3B & 3C).

Example 2

Figure 4:
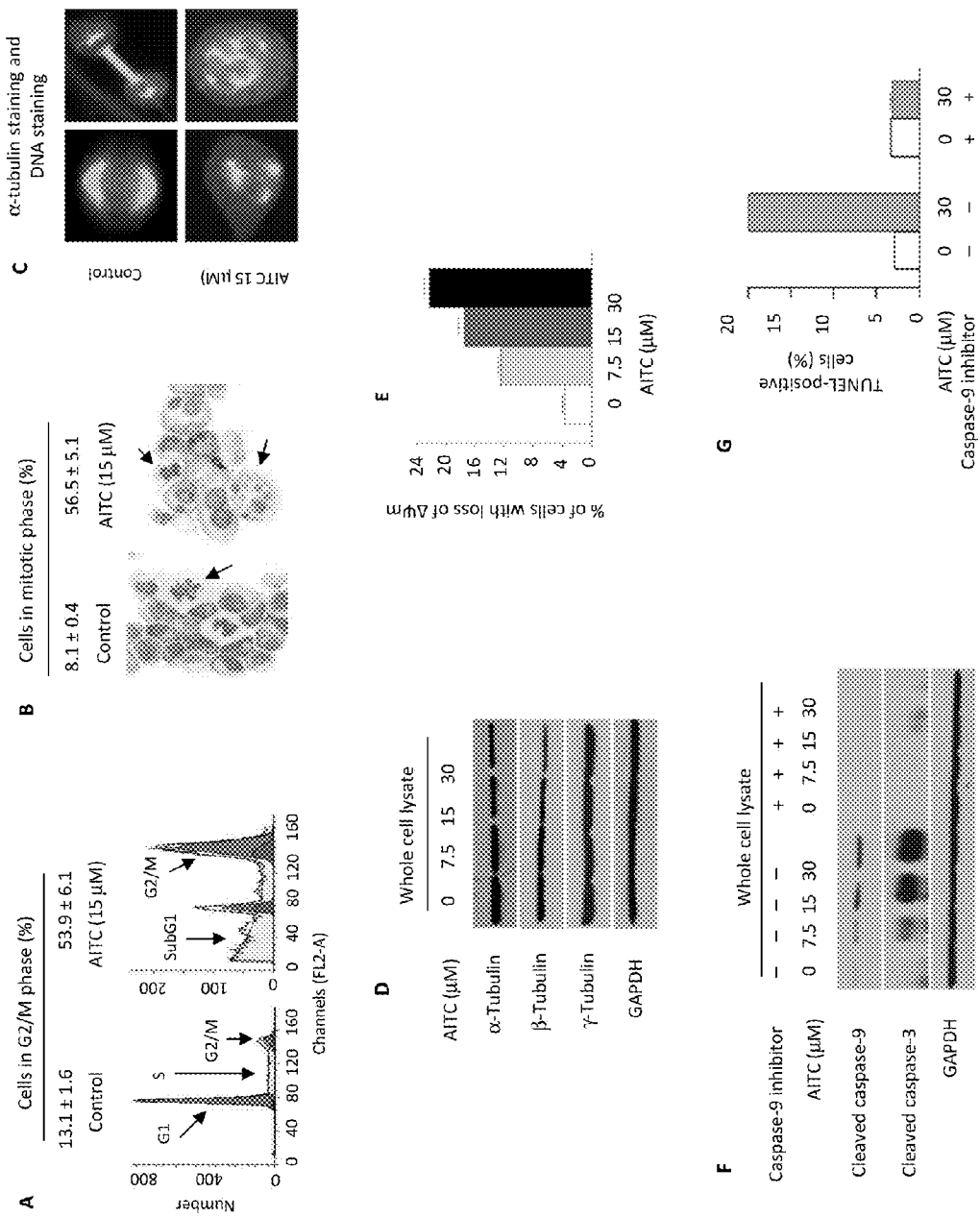
FIG. 4. Effect of AITC on mitosis, tubulin expression and apoptosis in human bladder cancer UM-UC-3 cells. Cells were treated with vehicle or AITC for 24 h (each numerical value is mean±SD). A. Flow cytometry analysis for cell cycle arrest. B. Wright-Giemsa staining for counting mitotic figures. Arrows point to cells in mitosis or mitotic catastrophe. C. Immunofluorescent staining of microtubules (green color) and DNA staining with DAPI (blue color). D. Western blotting of tubulins (GAPDH as a loading control). E. Loss of mitochondrial transmembrane potential (Δψm) measured by flow cytometry. F. Western blotting of caspase-9 and caspase-3 (GAPDH as a loading control). G. Apoptotic cells (TUNEL cells) measured by flow cytometry. Cells in F and G were co-treated with or without 20 microM Z-LEHD-FMK (a caspase-9 inhibitor).

This Example demonstrates that AITC targets α-tubulin and β-tubulin and arrests cells in mitosis and activates mitochondria-mediated apoptosis. Comparison of UM-UC-3 cells that were arrested in G2/M phase by AITC as measured by flow cytometry (FIG. 4A) with those arrested in mitosis by AITC as measured by Wright-Giemsa staining showed that AITC arrested cells almost exclusively in mitosis (FIG. 4B). Moreover, many AITC-treated cells showed multiple micronuclei, indicative of mitotic catastrophe. Simultaneous immunostaining of α-tubulin (green color) and DNA staining with 4',6-diamidino-2-phenylindole (DAPI, blue color) showed control cells undergoing typical mitosis and cell division (bipolar mitotic spindle and separation of sister chromosomes), whereas AITC-treated cells exhibited aberrant and multi-polar mitotic spindle and lack of separation of sister chromosomes (FIG. 4C), reminiscent of the effects of vincristine (a microtubule depolymerizer) and taxol (a microtubule stabilizer) [17]. However, AITC does not appear to affect tubulin polymerization, as AITC had no effect on the rate of tubulin polymerization in an in vitro assay (result not shown). In contrast, AITC significantly down regulated both α-tubulin and β-tubulin, but not γ-tubulin (FIG. 4D), suggesting that α-tubulin and β-tubulin may be key AITC targets for mitotic arrest. Further experiments suggest that AITC destabilizes α-tubulin and β-tubulin proteins (result not shown). Our findings demonstrate that AITC is a new class of mitosis blocker, as its mechanism of action differs from that of taxol and vincristine. Moreover, we found that AITC caused a loss of mitochondrial transmembrane potential (FIG. 4E), release of cytochrome c from mitochondria to cytoplasm (result not shown), activation of both caspase-9 and caspase-3 (FIG. 4F), and formation of TUNEL-positive cells (FIG. 4G), and that the caspase-9 inhibitor Z-LEHD-FMK completely blocked AITC-caused activation of the caspases and formation of TUNEL-positive cells. These results show that AITC kills bladder cancer cells by causing mitotic arrest and activating the mitochondria-mediated apoptosis pathway.

Example 3

This Example demonstrates that SF down regulates Cox-2 in human bladder cancer cells. Cox-2 is a well-known oncogene, is over expressed in the majority of human bladder cancers, and is considered a major drug target in bladder cancer therapy. We show that SF strongly down regulates Cox-2 in cultured human bladder cancer cells that overexpress Cox-2 (FIG. 5), by destabilizing Cox-2 mRNA (data not shown). However, the inhibitory effect of AITC on Cox-2 was not detectable (FIG. 5).

Example 4

Figure 6:
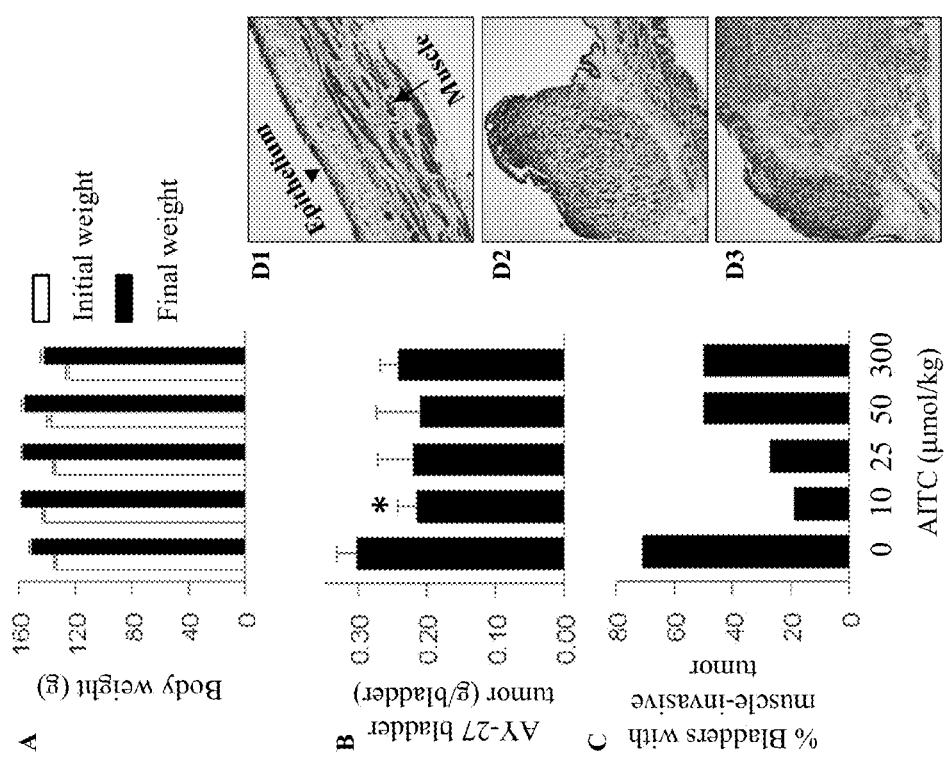
FIG. 6. Inhibition of bladder cancer development by AITC. Female F344 rats were inoculated intravesically with bladder cancer AY-27 cells to initiate development of orthotopic bladder tumor. Oral administration of AITC at 0, 10, 25, 50 and 300 micromols/kg once daily was started 1 day after AY-27 cell inoculation and ended 3 weeks later. The number of rats per group varied from 6 to 33; some of the data, particularly the control group (n=33) and the group treated with the lowest dose of AITC (n=23), were pooled from several experiments. A. The initial and final body weights. B. The weights of bladder tumors. Bladder tumor weight was calculated by subtracting the average normal bladder weight from tumor-bearing bladder weight. *P<0.05. C. Percentage of bladders where the tumor invaded the muscle tissue. D. H/E staining of the normal rat bladder wall (D1), a superficial rat bladder tumor (D2), and a rat bladder tumor that invaded the muscle layer (D3).

This Example demonstrates the inhibition of bladder cancer growth in vivo by performing an embodiment of the invention. AITC was evaluated in an orthotopic rat bladder cancer model. Within 3 weeks after intravesical instillation of $1 \times 10^6$ AY-27 cells, the tumors weighed on average 0.30 g, which was ~4.4 times the normal bladder weight. Daily oral administration of AITC was initiated one day after instillation of AY-27 cells and continued for 3 weeks. AITC was evaluated at 4 dose levels: 10, 25, 50 and 300 micromols/kg. There was no treatment related adverse effect as reflected by no weight loss in the animals (FIG. 6A). AITC at 300 micromols/kg inhibited orthotopic bladder cancer growth by 20% but it became somewhat more efficacious at the lower dose levels, inhibiting tumor growth by 30%, with its effect at 10 micromols/kg showing statistical significance (P=0.034) (FIG. 6B). Histological examination of the tumors showed increasing inhibition of muscle invasion with decreasing AITC dose (FIG. 6C). Only 18.9% of the tumor-bearing bladders showing muscle invasion in rats treated with AITC at 10 micromols/kg, compared to 27% in rats treated with AITC at 25 micromols/kg, 50% in rats treated with AITC at 50 or 300 micromols/kg, and 71% in the control rats, (FIG. 6C). FIG. 6D depicts representative images of normal rat bladder wall (D1), a superficial AY-27 rat bladder tumor (D2), and a muscle-invasive AY-27 rat bladder tumor (D3).

Example 5

Figure 7:
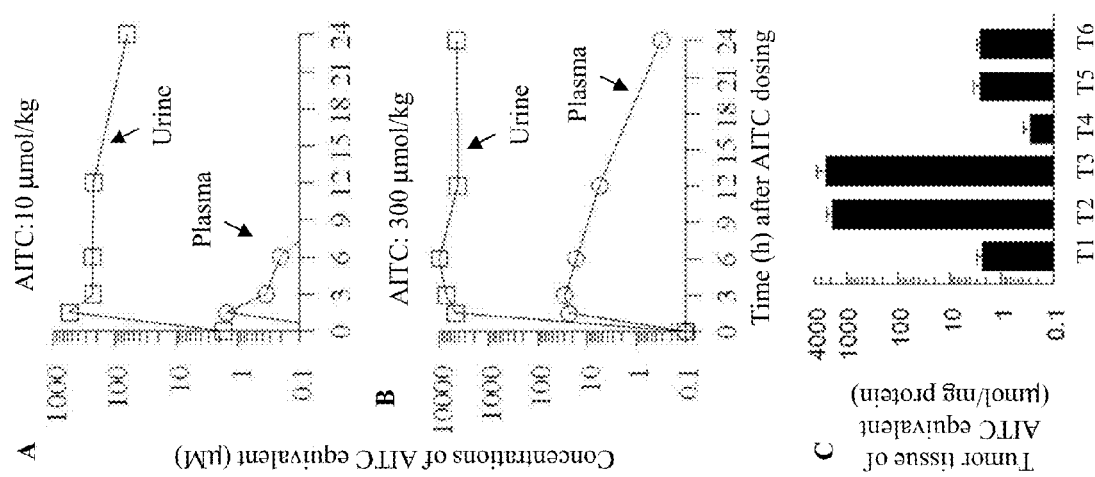
FIG. 7. Pharmacokinetics of AITC in F344 rats. A & B. Five groups of 4-6 female rats were administered a single oral dose of AITC at 10 or 300 micromols/kg and then kept in metabolism cages for urine collection (1 rat/cage) for 1.5, 3, 6, 12 and 24 h. At the end of each time period, blood was drawn from one group of rats, from which plasma was prepared. C. Rats bearing orthotopic bladder tumors, 3 weeks after AY-27 cell inoculation, were administered a single oral dose of AITC at 300 micromols/kg. Orthotopic tumors were removed from the rats at 0 h (T1), 1.5 h (T2), and 6 h (T3) after AITC dosing. Concentrations of AITC equivalent in plasma, urine and tumor tissue homogenates were determined by the cyclocondensation assay developed in our lab. Each value is a mean±SE.

This Example demonstrates AITC levels in the plasma, urine and tumor tissues. Rats were administered a single oral dose of AITC at 10 or 300 micromols/kg, and urine and blood were collected at several time intervals up to 24 h. Cyclocondensation assay was used for measurement of AITC equivalent in the samples [12]. Oral administration of AITC led to dose-dependent increase in the levels of AITC equivalent in both plasma and urine (FIGS. 7A & 7B). Peak plasma concentrations of AITC equivalent of 1.5 microM and 23.4 μM were reached within 3 h of AITC dosing at 10 and 300 miromols/kg, respectively. Corresponding urinary concentrations of AITC equivalent of 0.6 mM and 9.9 mM were reached within 6 h of dosing. The urinary peak concentrations of AITC equivalent were 400-423 fold higher than that in the plasma. Moreover, while the plasma concentrations of AITC equivalent declined rapidly thereafter (half life of less than 3 h at the low AITC dose and approximately 6 h at the higher dose), urinary concentrations of AITC equivalent declined slowly. For example, the average 24-h urinary concentrations of AITC equivalent were 63.8 microM (low AITC dose) and 4.5 mM (high AITC dose), which were 11.6-45.2% of the peak urinary concentrations, but were 4,911-14,501 fold higher than corresponding plasma concentrations at 24 h after dosing.

Low basal levels of AITC equivalent were detected in orthotopic tumors (2.4 micromols/mg protein) (FIG. 7C) possibly due to the rat diet containing a trace amount of AITC or related compounds. Levels of AITC equivalent in the orthotopic bladder tumors were 1.9 and 2.5 millimoles/mg protein at 1.5 and 6 h after the rats were given a single oral dose of AITC at 300 micromols/kg, which were 790-1,071 times higher than the basal level. These data show clearly that orally administered AITC is selectively delivered to the cancer tissue in the bladder through urinary excretion.

In summary, orally administered AITC was shown to have potent anticancer activity in terms of significantly being delivered and concentrated in urine and bladder cancer tissues within 24 hours of oral administration; inhibiting bladder cancer growth; preventing bladder muscle invasion and thus retarding bladder cancer metastasis. These data demonstrate the efficacy of delivering compositions of the invention into the urinary bladder where it is active and available at a concentration that is able to selectively target malignant cells while sparing normal cells. In addition, we have shown that SF is also selectively delivered to bladder tissue through urinary excretion [18].

Example 6

This Example demonstrates that sinigrin itself is not bioactive. Glucosinolates such sinigrin and glucoraphanin are the precursors of ITCs in cruciferous vegetables and their seeds such as mustard seed powder, horseradish powder and wasabi powder etc. Glucosinolates are converted to various ITCs by myrosinase. Sinigrin is a specific precursor of AITC. Sinigrin by itself was found to be inactive in vitro on bladder cancer cell lines such as UM-UC-3 and AY-27 and needed the presence of enzyme myrosinase (thus converting to AITC) to give results similar to AITC (result not shown). Intestinal microflora which possesses some myrosinase activity may partially convert sinigrin to AITC in vivo. However, our analysis showed that only 3-5% of sinigrin was converted to AITC in rat in vivo, and that sinigrin was ineffective in the orthotopic rat bladder cancer model in vivo]. This suggests that consuming sinigrin or sinigrin-containing natural products (without accompanying myrosinase) may not deliver the full benefit of AITC, if sinigrin is not hydrolyzed to AITC. The present invention addresses this problem.

Example 7

Figure 8:
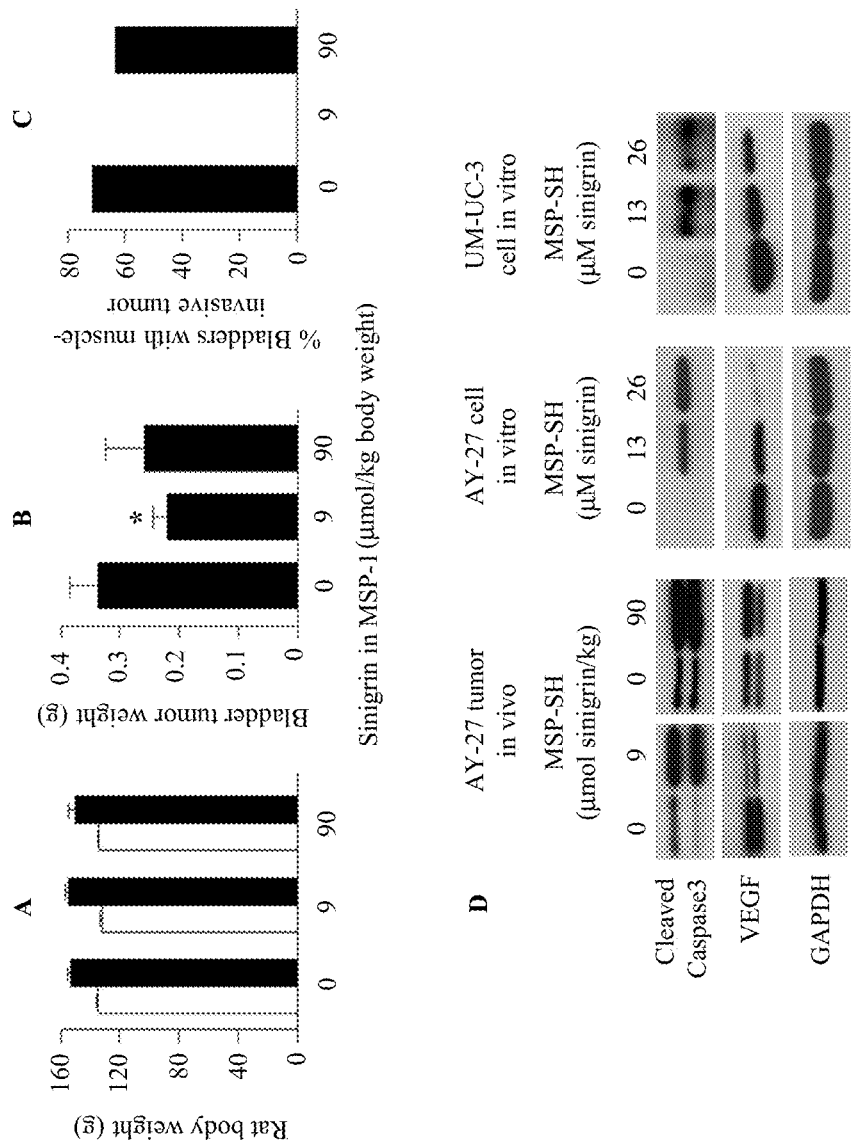
FIG. 8. Inhibition of bladder cancer development by MSP-1. Female F344 rats were inoculated with AY-27 cells intravesically via a urethra catheter to initiate development of orthotopic bladder cancer. Oral administration of MSP-1 of vehicle (water) once daily was started 1 day after cancer cell inoculation and ended 3 weeks later. The number of rats per group varied from 11-29. A. Initial (□) and final (■) body weights. B. Tumor weight was calculated by subtracting the average normal bladder weight from tumor-bearing bladder weight. *P<0.05. Each value in A and B is mean±SEM. C. Percentage of bladder where the tumor invaded the muscle tissue. D. The effects of MSP-1 on selected anticancer targets in UM-UC-3 cells (in vitro), AY-27 cells (in vitro) and AY-27 tumors (in vivo). The cells were treated with MSP-1 at the sinigrin concentrations of 13 and 26 microM for 24 h. The bladder tumors were removed from rats treated with MSP-1 at the sinigrin doses of 9 or 90 micromols/kg once daily for 3 weeks, started 1 day after cancer cell inoculation. Cell lysates and tumor homogenates were analyzed by Western blotting, using GAPDH as a loading control.

This Example demonstrates that mustard seed powder is a potent anti-bladder cancer substance. Our data demonstrate that cruciferous vegetables such as wasabi powder, horseradish powder and mustard seed powder contained vastly different amount of sinigrin/AITC. With respect to mustard seed, for some of our analyses, we analyzed a commercially available mustard seed powder (MSP-1), which was purchased from Spice House (Chicago, Ill.). We showed it contains sinigrin at 129 micromols/g. From our analysis it is believed that no AITC is present in the powder, but enough morosinase is present in the powder to allow apparently full conversion of sinigrin to AITC upon hydration both in vitro and in vivo. Our analysis of the powder stored at room temperature indicated that sinigrin in this powder is stable for at least 2 years. In the orthotopic rat bladder cancer model as described above, this substance had no effect on body weight gain (FIG. 8A), but inhibited bladder cancer growth by 35% at a sinigrin dose of 9 micromols/kg and 23% at the sinigrin dose of 90 micromols/kg (FIG. 8B), and inhibited muscle invasion completely at the sinigrin dose of 9 micromols/kg and 13% at the sinigrin dose of 90 micromols/kg (FIG. 8C). Thus, MSP-1 was more effective at the low dose than at the high dose. However, further decrease in MSP-1 dose resulted in lower anticancer efficacy. More interestingly, on an equimolar basis, the anticancer activity of AITC delivered as the mustard seed powder was more potent than that of pure AITC. Moreover, MSP-1 caused strong activation of caspase-3 and reduced vascular endothelial growth factor (VEGF) level in both cultured bladder cancer cells and bladder tumors in vivo (FIG. 8D). VEGF is a major tumor angiogenesis stimulator. Both caspase-3 and VEGF are anticancer targets. Interestingly, MSP-1 was effective against VEGF in vivo only at the low dose, suggesting that VEGF may be a key target in the inhibition of tumor muscle invasion by MSP-1.

Example 8

Figure 9:
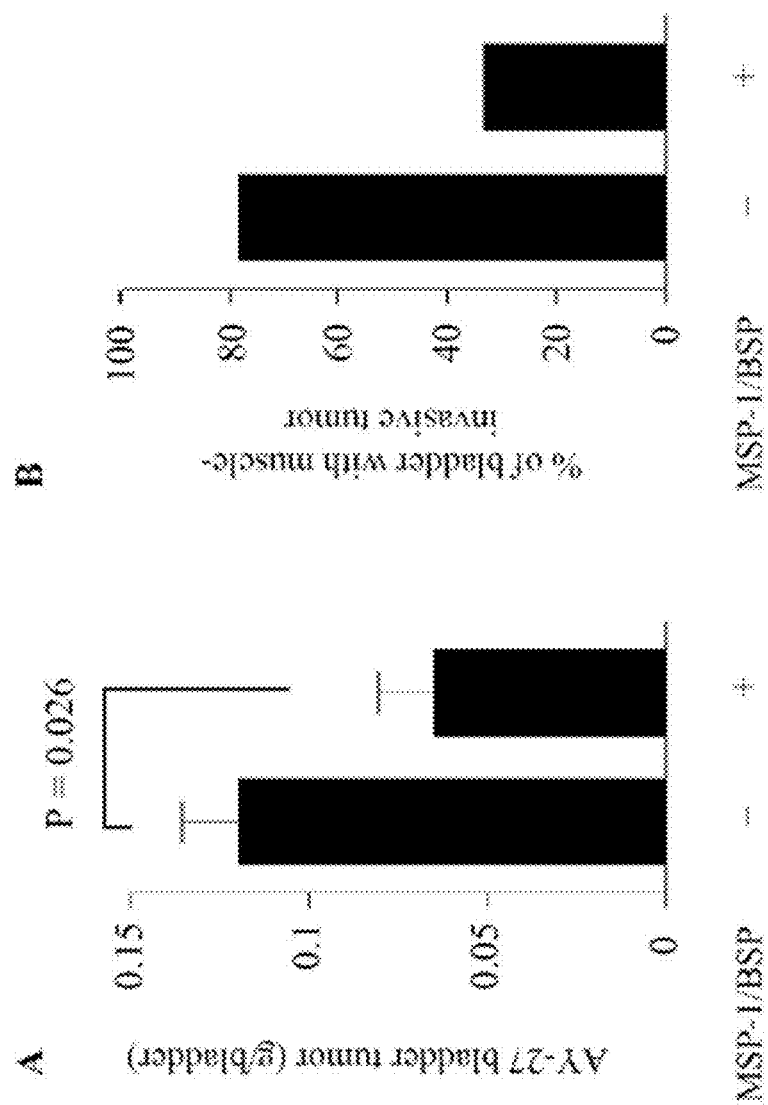
FIG. 9. Inhibition of bladder cancer development by a mixture of MSP-1 and a broccoli seed powder (BSP) (MSP-1:BSP=1:1). Female F344 rats were inoculated with bladder cancer AY-27 cells to initiate development of orthotopic bladder tumor. Oral administration of the powder (sinigrin and glucoraphanin: each at 10 micromols/kg) once daily was started 1 day after AY-27 cell inoculation and ended 3 weeks later. The number of rats per group was 9-10. Each value is mean±SE.

This Example demonstrates that a mixture of MSP-1 and broccoli seed powder inhibits bladder cancer development. Glucoraphanin-rich broccoli seeds (cultiva SAGA) were purchased from Caudill Seed (Louisville Ky.), baked and then autoclaved as described above to inactivate ESP (myrosinase is also believed to be inactivated in the process) and then ground into a fine powder. Removing ESP is believed to be important to maximize conversion from glucosinolates to ITC, as SF yield increased 27%, from 60 micromols per gram of regular seeds (powder) to 76 micromols per gram of heat-treated seeds (powder). This powder was mixed with MSP-1 (approximately 1:1). The mixture contains glucoraphanin and sinigrin as well as myrosinase (carried by MSP-1). Upon hydration or ingestion, the myrosinase in the powder apparently fully converts glucoraphanin and sinigrin to SF and AITC (data not shown). We have demonstrated that the mixed powder inhibits bladder cancer development in vivo in the same orthotopic rat bladder cancer model which was used to assess AITC and MSP-1. Rats were fed with the powder at the sinigrin and glucoraphanin doses of 10 micromols/kg each once daily for 3 weeks. Bladder tumor growth was inhibited 46% (FIG. 9A), which was more significant than MSP-1 alone, which at the sinigrin dose of 9 micromols/kg inhibited tumor growth by 35% (FIG. 8B). Moreover, the combination treatment also strongly inhibited muscle invasion of bladder cancer (FIG. 9B). It is noteworthy that AY-27 cells do not over express Cox-2 (result not shown), and the anticancer efficacy of SF may not be fully demonstrable in this animal model. Thus, it is expected that the method of the invention will be more effective in humans who have bladder cancer.

Example 9

It is disclosed above that ITCs are metabolized primarily through the mercapturic acid pathway in vivo resulting in the formation of N-acetylcysteine (NAC) conjugates which are excreted through urine. The NAC conjugates dissociate to the parent ITCs when stored in the urine in the bladder and in this manner act as prodrugs of ITCs. In various embodiments, the compositions and methods of the invention include providing an ITC as a thiol conjugate or a derivative thereof. In one embodiment, a derivative of the thiol conjugate is an N-acetylcysteine conjugate. In one embodiment, the NAC-conjugate is N-acetyl-S—(N-allylthiocarbamoyl) cysteine, more commonly known as the N-acetylcysteine conjugate of AITC (NAC-AITC; see FIG. 10A for its chemical structure).

This Example demonstrates that NAC-AITC inhibits the survival and proliferation of bladder cancer cells, that NAC-AITC inhibits bladder cancer growth in vivo, and that NAC-AITC is selectively delivered to bladder through urinary excretion. In particular, this Example demonstrates that treatment of human bladder cancer UM-UC-3 cells or rat bladder cancer AY-27 cells with NAC-AITC at 15 µM results in significant inhibition of cell growth and proliferation, together with cell cycle arrest and apoptosis. We also show that NAC-AITC administered orally at 10 µmol/kg body wt inhibits cancer growth by 40% and muscle invasion by 49% in an orthotopic rat bladder cancer model. Furthermore, the anticancer activity of NAC-AITC is associated with the modulation of several important molecular targets, including downregulation of both α-tubulin and β-tubulin, activation of caspase-3 and downregulation of vascular endothelial growth factor. These results are consistent with the understanding that NAC-AITC is a carrier of AITC. Furthermore, comparison of the pharmacokinetic and physical properties of NAC-AITC with those of AITC suggests that NAC-AITC is superior to AITC for potential use for prevention and therapy of bladder cancer, and for use as a nutraceutical.

The following materials and methods were used to obtain the data presented in this Example.

Materials. AITC was purchased from Sigma-Aldrich (St Louis, Mo.). NAC-AITC was synthesized and purified by the method of Vermeulen et al [11], using re-distilled AITC and N-acetyl cysteine (Sigma-Aldrich), and verified by mass spectrometry. The syntheses of AITC metabolites including the glutathione conjugate (GS-AITC), the cysteinylglycine conjugate (Gly-Cys-AITC) and the cysteine (Cys-AITC), followed a similar strategy. Antibodies specific for cleaved caspase-3, cleaved caspase-9 and β-tubulin were purchased from Cell Signaling Technology (Beverly, Mass.). Antibodies for β-tubulin, VEGF and glyceraldehyde 3-phosphate dehydrogenase (GAPDH) were purchased from EMD/Calbiochem (Gibbstown, N.J.), Santa Cruz Biotechnology (Santa Cruz, Calif.) and Millipore (Bellerica, Mass.), respectively.

Cells and Animals. Human bladder cancer UM-UC-3 cell line and rat bladder cancer AY-27 cell line were used in the study; their origin and culture condition have been previously reported [3]. Female F344 rats were purchased from Harlan Laboratories (Indianapolis, Ind.) and were acclimatized for ~1 week before experiments. The animals were maintained at 21-23° C. and a 12 h light/dark cycle with free access of food (Harlan Teklad LM-485 mouse/rat sterilizable diet) and water. All animal protocols and procedures were approved by the Roswell Park Cancer Institute Animal Care and Use committee.

Assays for cell proliferation, cell cycle arrest and apoptosis. To determine the antiproliferative activity of NAC-AITC, AY-27 cells were grown in 96-well microtiter plates ($5\times10^6$ cells with 0.15 ml medium per well) for 24 h and then grown for 72 h in fresh medium (0.2 ml/well) containing a series of concentrations of NAC-AITC or solvent. Cell growth was measured at the end of treatment using the 3-(4,6-dimethylthiazol-2-yl)-2,5-diphenyltetrazolium bromide assay, from which the half maximal inhibitory concentration ($IC_{50}$) of NAC-AITC was calculated. AITC was also evaluated for comparison.

The effect of NAC-AITC on cell cycle progression was measured by flow cytometry as described previously. Briefly, $1.5\times10^6$ AY-27 cells were grown in each 10-cm plate with 10 ml medium for 24 h and then treated with NAC-AITC or solvent for 24 h before analysis. Induction of apoptosis by NAC-AITC was measured using the Cell Death Detection ELISA$^{plus}$ kit (Roche Diagnostics, Indianapolis, Ind.), following the manufacturer's instruction. Briefly, cells were cultured in 96-well plates as described above and treated with NAC-AITC or solvent for 24 h. At the end of treatment, the cells were treated with lysis buffer, and after a low-speed centrifugation, a portion of the supernatant fraction was used for spectroscopic measurement (expressed as $A_{405-490\ nm}$) of cytoplasmic levels of histone-associated mononucleosomes or oligonucleosomes by an enzyme-linked immunosorbent assay. In all experiments, NAC-AITC was dissolved in DMSO and then diluted in water. The DMSO concentration in culture medium was ≤0.1%.

Using the above described materials and methods for this Example, the following results were obtained.

A syngeneic orthotopic rat bladder cancer model. The anticancer activity of NAC-AITC was evaluated in a syngeneic orthotopic rat bladder cancer model using conventional techniques, with a minor modification. Briefly, after priming the bladder mucosa with 0.3 ml of 0.1 N HCl for 15 s, followed first by treatment with 0.3 ml of 0.1 N KOH for 15 s to neutralize the acid and then phosphate-buffered saline wash, female F344 rats (8-10 weeks of age) were inoculated orthotopically via a catheter (BD Insyte™ Autoguard™ shielded IV catheter, 18 G×48 mm) through the urethra with AY-27 cells ($1\times10^6$ cells in 0.5 ml serum-free medium per rat). Female rats were used in the experiment because urethral catheterization in male rats is difficult. One day after the inoculation, the rats were randomly assigned to receive by gavage either vehicle (1.33 ml water containing 5% DMSO/kg body wt) or NAC-AITC in an equal volume of water/DMSO once daily for 3 weeks. NAC-AITC was freshly dissolved in DMSO and diluted in water. The animals were monitored daily and were euthanized 24 h after the last dose of NACAITC or vehicle; the bladders were quickly removed, and after opening, were examined for macroscopic lesions, weighed and photographed with a digital camera. Tumor was present in all the bladders; tumor weight was calculated by subtracting the average normal bladder weight (from untreated rats at the same age) from the tumor-bearing bladder weight. Some bladders that showed significant edema/inflammation were excluded to ensure accurate measurement of tumor weight. Approximately, half of each bladder was fixed in formalin for histological analysis and the other half was frozen in liquid nitrogen for western blot analysis.

Measurement of pharmacokinetic profiles of AITC and NAC-AITC. The experiment was carried out in female F344 rats since these animals were used in the rat bladder cancer model described above. Groups of three to five rats (8-9 weeks of age) were given a single oral dose of AITC, NAC-AITC or vehicles. AITC was administered in 0.5 ml of soy oil per rat, whereas NACAITC was dissolved in DMSO and diluted with water and administered in 0.2 ml volume (5% DMSO) per rat. The rats were immediately transferred to metabolism cages (one rat per cage), with free access to food and water, for urine collection over four consecutive periods of 0-1.5, 1.5-3, 3-6 and 6-24 h. Additional groups of female F344 rats that were treated with the same doses of AITC, NAC-AITC or the vehicles were used for blood drawing, to avoid potential impact of blood loss on the pharmacokinetics of the compounds. One group of animals was killed at 1.5, 3, 6 and 24 h after dosing for blood collection and plasma preparation.

AITC and NAC-AITC contents in the plasma and urine were determined using the high-performance liquid chromatography (HPLC)-based cyclocondensation assay, and are expressed as AITC equivalent or NAC-AITC equivalent. The cyclocondensation assay detects AITC, NAC-AITC and other metabolites of AITC formed in the mercapturic acid pathway.

To specifically measure urinary levels of NAC-AITC, groups of five rats were dosed orally with either AITC or NAC-AITC at 300 μmol/kg and immediately moved to metabolism cages (one rat per cage) for 24 h urine collection. AITC and NAC-AITC were freshly prepared in soy oil or 5% aqueous DMSO, as described above. Urine samples were fractionated by HPLC, using an Agilent system with a diode-array detector, to separate NAC-AITC from AITC and other metabolites including GS-AITC, Gly-Cys-AITC and Cys-AITC before analysis of the fractions by the cyclocondensation assay. The mobile phase consisted of acetonitrile and 20 mM aqueous potassium phosphate (pH 3). The system was operated at a flow rate of 1.75 ml/min, using a Partisil 100DS-2 reverse-phase column (4.6×250 mm; Whatman), beginning with an isocratic phase of 15% acetonitrile for 15 min, followed by 100% acetonitrile for 5 min. The compounds were monitored at both 230 nm (AITC) and 254 nm (its metabolites). Pure synthetic standards were used to set up the HPLC conditions and to establish retention times for each compound; GS-AITC, Gly-Cys-AITC, Cys-AITC, NAC-AITC and AITC eluted at 3.3, 4.4, 6.5, 8.9 and 19.5 min, respectively. The fraction corresponding to NAC-AITC was collected and quantified by the cyclocondensation assay; its identity was confirmed by infusion electrospray ionization mass spectrometry.

Measurement of dissociation of NAC-AITC. The assay was based on a known protocol. Briefly, a solution of NAC-AITC was prepared as rapidly as possible by dilution of 0.2 ml of 5 mM NAC-AITC freshly prepared in 20 mM sodium phosphate buffer (pH 7.4): DMSO (1:1) with 20 mM sodium phosphate buffer (pH 7.4) to 10 ml, resulting in a 0.1 mM NAC-AITC solution in 1% DMSO. An aliquot (0.05 ml) was immediately analyzed by HPLC; the remainder of the solution was incubated at 37° C. on a shaker, and an aliquot (0.05 ml) was analyzed by HPLC at different time points up to 24 h. The HPLC condition was the same as used in the urine analysis described above. A plot of the conjugate peak area remaining versus time was generated to determine the half-time of decomposition.

Western blot analysis. Cells after harvest were washed with ice-cold phosphate-buffered saline, suspended in radioimmunoprecipitation assay lysis buffer supplemented with a protease inhibitor cocktail (Sigma-Aldrich) and further lysed by sonication. Tissue specimens were washed with ice-cold phosphate-buffered saline and homogenized in radioimmunoprecipitation assay lysis buffer supplemented with the protease inhibitor cocktail in glass homogenizers. After removal of the debris from both cell lysates and tissue homogenates by centrifugation and measurement of protein contents by a bicinchoninic acid protein assay kit (Pierce, Rockford, Ill.), the samples were resolved by sodium dodecyl sulfate-polyacrylamide gel electrophoresis (8-12%), followed by transfer to polyvinylidene difluoride membranes. The membranes were then probed by a specific antibody and stained using SuperSignal West Pico Chemiluminescence detection system (Thermo Scientific, Rockford, Ill.).

Histological analysis. Rat bladder specimens fixed in formalin were paraffin embedded, cut at ~4 μm and stained with hematoxylin and eosin. The slides were examined for bladder and tumor histology using a Nikon 50i light microscope.

Statistical analysis. All numerical values are presented as mean±SE. The difference between the means of two groups was analyzed for statistical significance using unpaired two-tailed Student t-test. One-way analysis of variance was used for multigroup comparison, followed by Dunnett's multiple comparison test. P>0.05 was considered significant.

Based on the materials and methods as described above in this Example the following results were obtained.

Figure 10:
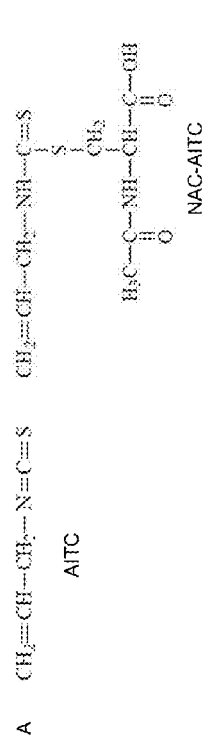
FIG. 10. The effect of NAC-AITC on cell survival and proliferation. NAC-AITC was evaluated in both UM-UC-3 cells and AY-27 cells. (A) Chemical structures of AITC and NAC-AITC. (B) Cell growth and proliferation, measured by 3-(4,6-dimethylthiazol-2-yl)-2,5-diphenyltetrazolium bromide assay, 72 h treatment with AITC or NAC-AITC at indicated concentrations. $IC_{50}$ was calculated from the nonlinear regression curve fit. (C) Apoptosis, measured by an enzyme-linked immunosorbent assay, 24 h NAC-AITC treatment at 15 lM. (D) Cell cycle (open bars, G1; shaded bars, S; closed bars, G2/M), measured by flow cytometry, 24 h NAC-AITC treatment at 15 μM. *P<, 0.005, compared with control.
Figure 10:
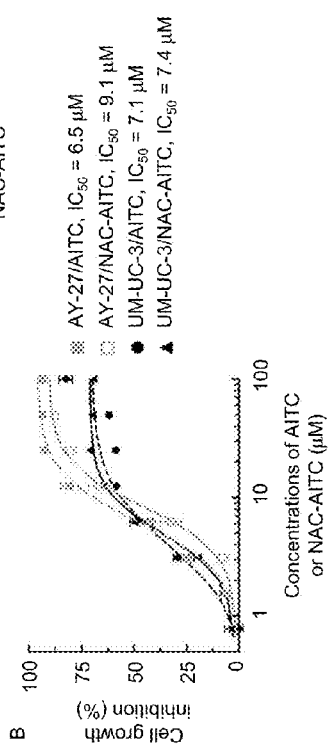
Figure 10:
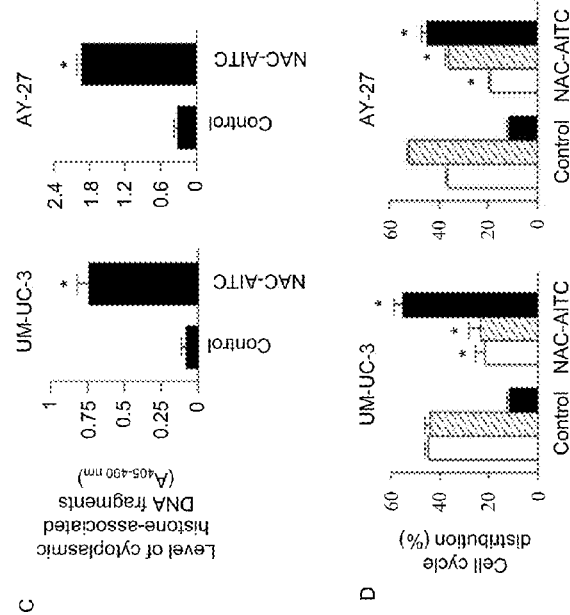
Figure 11:
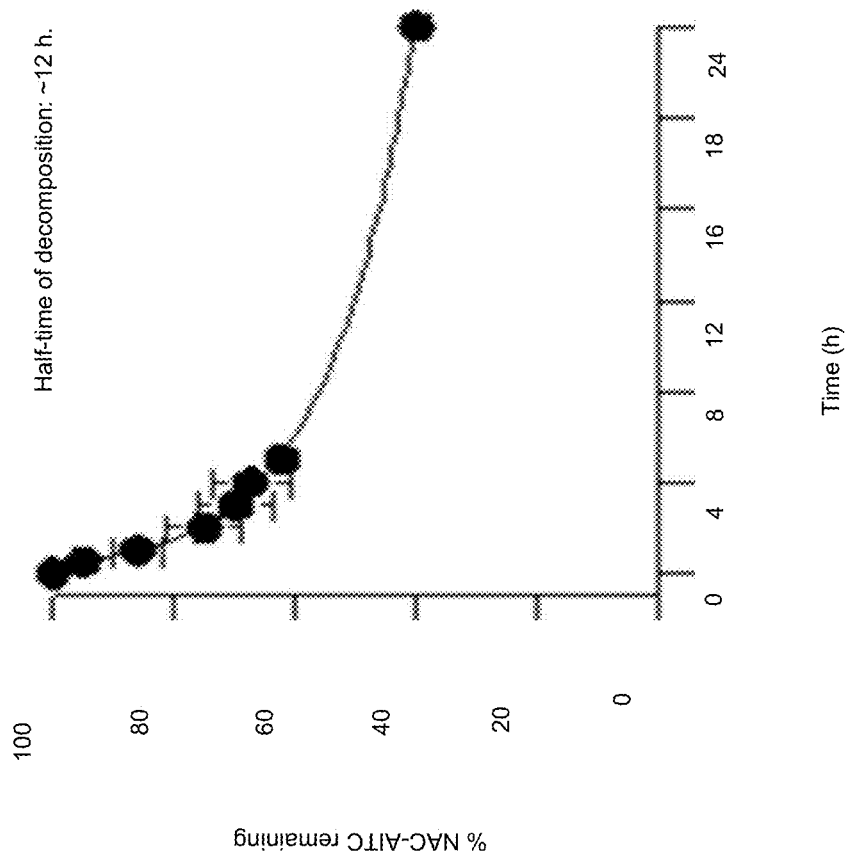
FIG. 11. Dissociation of NAC-AITC. NAC-AITC at 100 μM was freshly prepared in 20 mM sodium phosphate buffer (pH 7.4) containing 1% DMSO and incubated at 37° C. for 0, 0.5, 1, 2, 3, 4, 5 and 24 h. At each time point, an aliquot of the solution was analyzed for remaining NAC-AITC by HPLC. Each value is a mean±SD (n=3).

NAC-AITC inhibits the survival and proliferation of bladder cancer cells. Treatment of UM-UC-3 and AY-27 cells with NAC-AITC led to dosedependent inhibition of cell proliferation, with an $IC_{50}$ value of 7.4 μM in UM-UC-3 cells and 9.1 lM in AY-27 cells; AITC itself was of similar efficacy (FIG. 10B). Inhibition of cell proliferation by NAC-AITC was associated with significant cell cycle arrest and induction of apoptosis. Treatment of UM-UC-3 and AY-27 cells with NAC-AITC at 15 μM for 24 h resulted in 8.8- and 10.6-fold increase in apoptotic activity, respectively (FIG. 10C). Cells were arrested by NAC-AITC in the G2/M phase; 55% UM-UC-3 cells and 45% AY-27 cells were detected in $G_2$/M phase after treatment with NAC-AITC at 15 lM for 24 h compared with only 11-12% of control cells present in this phase (FIG. 10D). The effects of NAC-AITC on cell cycle and apoptosis were similar to those recorded with AITC. Previous studies have suggested that N-acetylcysteine conjugates of isothiocyanates, including NAC-AITC, are not biologically active themselves and cannot be taken up by cells, but serve as the carriers of their parent compounds. Indeed, the half-time of dissociation of NAC-AITC in phosphate buffer (pH 7.4, 37° C.) was ~12 h (FIG. 11). However, we found that NAC-AITC when kept dry was completely stable for at least 16 months at room temperature (data not shown).

Figure 12:
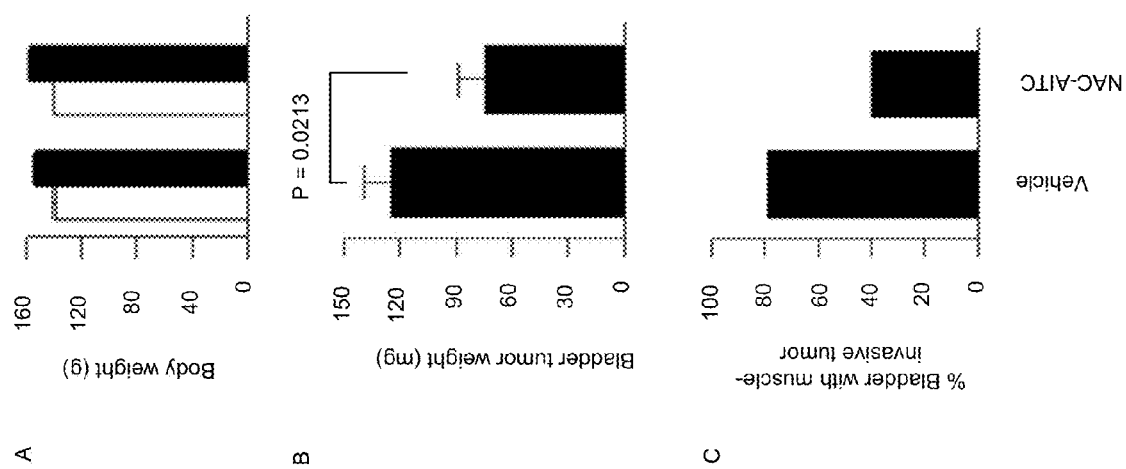
FIG. 12. Inhibition of bladder cancer development by NAC-AITC. Bladder cancer was initiated in female F344 rats by orthotopic inoculation of bladder cancer AY-27 cells. Oral administration of NAC-AITC at 10 μmmol/kg body wt once daily was started 1 day after cancer cell inoculation and ended 3 weeks later. There were 23 rats in the control group and 15 rats in the treatment group. (A) The initial (open bars) and final (closed bars) body weight. (B) Bladder tumor weight. Each value is a mean±SE. (C) Percentage of bladders where the tumor invaded the muscle tissue.

NAC-AITC inhibits bladder cancer growth in vivo. NAC-AITC was next evaluated in an orthotopic rat bladder cancer model. AITC is known to significantly inhibit bladder cancer growth and muscle invasion in this model. Bladder cancer AY-27 cells were inoculated intravesically via a urethral catheter. Daily oral administration of NAC-AITC at 10 μmol/kg body wt was initiated 1 day after AY-27 cell inoculation and continued for 3 weeks. The same dose and treatment time were previously used when AITC was evaluated in the same animal model. All rats behaved normally during NAC-AITC treatment, and no significant effect on body weight was detected (FIG. 12A). All rats developed bladder tumors, but treatment with NAC-AITC inhibited tumor growth by 40% (FIG. 12B). Moreover, although 79% of the bladders in the control group showed tumor invasion into the musculature, muscle invasion occurred in only 30% of the bladders in the NAC-AITC group (FIG. 12B). In comparison, AITC, which was previously evaluated in the same animal model at the same dose level and treatment duration, inhibited tumor growth and muscle invasion by 30 and 73%, respectively. Thus, the anticancer efficacy of NAC-AITC is similar to that of AITC.

Figure 13:
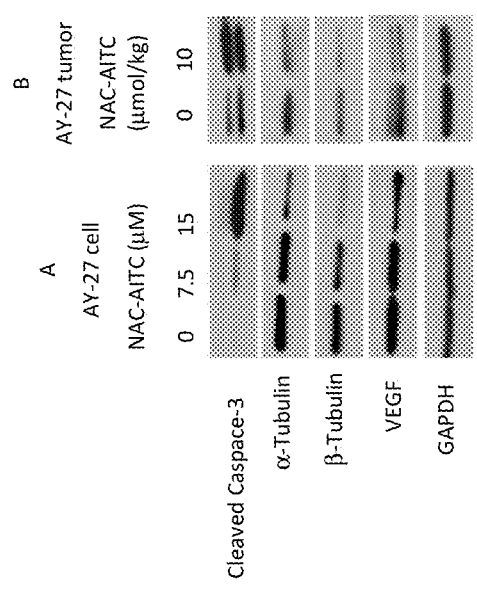
FIG. 13. Molecular targets of NAC-AITC in bladder cancer. AY-27 cells in culture were treated with NAC-AITC for 24 h. The results are representative of at least two experiments. The bladder tumors were removed from rats, which were treated with NAC-AITC orally at 10 μmol/kg once daily for 3 weeks, starting 1 day after intravesicular inoculation of AY-27 cells. The results are representative of three to five tumors assayed in each group. Cell lysates and tumor tissue homogenates were analyzed by western blot analysis, using GAPDH as a loading control.

We examined the effect of NAC-AITC on several proteins which are known to play important roles in cancer cell survival, proliferation and invasion, including caspase-3, α-tubulin, β-tubulin and VEGF. Treatment of AY-27 cells with NAC-AITC at 7.5 and 15 μM caused dose-dependent cleavage/activation of caspase-3 and downregulation of α-tubulin, β-tubulin and VEGF (FIG. 13A). Moreover, similar changes in these proteins were also detected in bladder tumors removed from rats treated with NAC-AITC at 10 μmol/kg (FIG. 13B). The results described above make it clear that NAC-AITC replicates the anticancer mechanism of AITC.

NAC-AITC is selectively delivered to bladder through urinary excretion. We have also compared the pharmacokinetic profiles of NAC-AITC and AITC as shown in Table 1.

TABLE 1

Pharmacokinetic profiles of NAC-AITC and AITC

| | Plasma | | Urine | |
|---|---|---|---|---|
| Rat treatment | Time (h) | AITC or NAC-AITC equivalent (μM) | Time (h) | AITC or NAC-AITC equivalent (μM) |
| Control[#] | | <0.5 | | <0.2 |
| NAC-AITC (10 μmol/kg) | 1.5 | 1.2 ± 0.3 | 0-1.5 | 398 ± 118 |
| | 3 | 0.7 ± 0.2 | 1.5-3 | 1510 ± 101[a] |
| | 6 | <0.5 | 3-6 | 337 ± 99.3[b] |
| | 24 | <0.5 | 6-24 | 16.6 ± 1.1 |
| AITC (10 μmol/kg) | 1.5 | 1.5 ± 0.2 | 0-1.5 | 115 ± 44.3 |
| | 3 | <0.5 | 1.5-3 | 415 ± 86.7[a] |
| | 6 | <0.5 | 3-6 | 744 ± 109[b] |
| | 24 | <0.5 | 6-24 | 34.7 ± 6.8 |

[#]Control animals were given vehicle, from which blood and urine were collected at corresponding times. Each value is mean ± SE (n = 5).
[a,b]The two values marked with the same alphabetic letter is statistically significant.

Total levels of AITC, NAC-AITC and other potential AITC metabolites formed in the mercapturic acid pathway were measured in blood and urine by the cyclocondensation assay and were expressed as AITC equivalent or NAC-AITC equivalent. In rats that were given a single oral dose of NAC-AITC (10 μmol/kg), the plasma concentration of NAC-AITC equivalent was 1.2 and 0.7 μM at 1.5 and 3 h post-dosing, respectively, and was undetectable by 6 h. In contrast, the average urinary concentrations of NAC-AITC equivalent were 398 and 1510 lM during the first 1.5 h and the 1.5-3 h interval after NAC-AITC dosing, respectively, which are 332- and 2157-fold higher than the plasma concentrations measured at 1.5 and 3 h, as mentioned above.

The average urinary concentration of NAC-AITC equivalent remained high at 337 µM, 3-6 h after the dosing, although it decreased 0.20-fold to 16.6 µM in the urine collected at 6-24 h after dosing.

The profound difference in concentrations of NAC-AITC equivalent between the plasma and urine in rats dosed with NAC-AITC, as described above, resembles that of AITC. In rats given a single oral dose of AITC (10 µmol/kg), the plasma concentration of AITC equivalent was 1.5 µM at 1.5 h post-dosing and was undetectable thereafter. In contrast, urinary concentrations of AITC equivalent ranged from 115-744 µM within 6 h of AITC dosing and decreased to 30 µM in the urine collected at 6-24 h after AITC dosing. Moreover, following treatment with NAC-AITC or AITC (a single oral dose at 10 µmol/kg), the 24 h cumulative urinary recovery for NAC-AITC and AITC in rats, as detected by the cyclocondensation assay, was 62.5±6.5% and 54.1±3.7% (mean±SE), respectively, and the difference is not statistically significant. Further analysis of urine samples by HPLC and mass spectrometry showed that NAC-AITC was the principal excretion product whether rats were given AITC or NAC-AITC. Hence, in the 24 h urine collected from rats given a single oral dose of AITC or NAC-AITC at 300 µmol/kg (a relatively high dose was used to facilitate detection of NAC-AITC), 85.8% of the urinary AITC equivalent and 83.3% of the urinary NAC-AITC equivalent were NAC-AITC, respectively (Table 2).

TABLE 2

Urinary recovery in rats given AITC and NAC-AITC

| | 24-h urinary recovery | | |
|---|---|---|---|
| | Total recovery*, | Recovered as NAC-AITC | |
| Rat treatment | % of administered dose | % of adminstered dose | % of total recovery |
| AITC | 54.8 ± 5.0 | 47.0 ± 9.3 | 85.8 ± 3.8 |
| NAC-AITC | 56.8 ± 3.1 | 47.3 ± 1.8 | 83.3 ± 4.5 |

*As AITC equivalent or NAC-AITC equivalent, measured by the cyclocondensation assay. Rats were given a single oral dose of AITC or NAC-AITC at 300 µmol/kg, followed by 24-h urine collection. Each value is a mean ± SE (3-5 rats per group). To measure NAC-AITC, urine samples were fractionated by HPLC, and the NAC-AITC fraction was then subjected to the cyclocondensation assay.

Orally dosed NAC-AITC was excreted in urine at a significantly faster rate than AITC, based on the comparison of their urinary concentrations at different time points, as shown in Table 1. Furthermore, the peak urinary concentration of AITC or NAC-AITC equivalent was reached at between 1.5 and 3 h following NAC-AITC dosing, but reached until 3 to 6 h after AITC administration.

In summary, both AITC and NAC-AITC after oral administration are rapidly excreted and concentrated in urine as NAC-AITC; urinary NAC-AITC serves as a carrier of AITC, which is ultimately responsible for bladder cancer inhibition in rats treated with AITC or NAC-AITC. Thus, NAC-AITC may be more preferable than AITC for potential bladder cancer prevention and therapy, although AITC can also be used according to the invention. NAC-AITC also has the advantage of being able to be provided as a stable gum with little odor. In this regard, we subsequently found that NAC-AITC could be readily formed into a tablet by conventional tableting technology and can thus, in certain embodiments, be provided as a component of the compositions of the invention in used in the methods of the invention accordingly. NAC-AITC is particularly attractive for potential use against recurrence of superficial bladder cancer, as it can be administered orally and delivers AITC to the bladder intravesicularly via urinary excretion. Moreover, for patients deemed to be at relatively low risk of cancer recurrence, no post-transurethral resection therapy is currently available, and for these individuals, NAC-AITC is expected to be a particularly valuable therapeutic.

REFERENCES

1. Kirkali Z, Chan T, Manoharan M, et al. Bladder cancer: epidemiology, staging and grading, and diagnosis. Urology 2005; 66: 4-34.
2. Cookson M S, Herr H W, Zhang Z F, Soloway S, Sogani P C, Fair W R. The treated natural history of high risk superficial bladder cancer: 15-year outcome. J Urol 1997; 158: 62-7.
3. Shahin O, Thalmann G N, Rentsch C, Mazzucchelli L, Studer U E. A retrospective analysis of 153 patients treated with or without intravesical *bacillus* Calmette-Guerin for primary stage T1 grade 3 bladder cancer: recurrence, progression and survival. J Urol 2003; 169: 96-100.
4. Pinkowish M D. Earlier use of aggressive therapy could prevent one-third of bladder cancer deaths. CA Cancer J Clin 2009; 59: 142-4.
5. Sonpavde G, Elfiky A A, Rosenberg J E. Novel agents for advanced bladder cancer. Therapeutic Advances in Medical Oncology 2009; 1: 13.
6. Raghavan D, Quinn D, Skinner D G, Stein J P. Surgery and adjunctive chemotherapy for invasive bladder cancer. Surg Oncol 2002; 11: 55-63.
7. Matusheski N, Juvik J A, Jeffery E H. Heating decreases epithiospecifier protein activity and increases sulforaphane formation in broccoli. Phytochem 2004; 65: 1273-1281.
8. Uematsu Y, Hirata K, Suzuki K, Iida K, Ueta T, Kamata K. Determination of isothiocyanates and related compounds in mustard extract and horseradish extract used as natural food additives. Shokuhin Eiseigaku Zasshi 2002; 43: $10^{-7}$.
9. Zhang Y, Talalay P, Cho C G, Posner G H. A major inducer of anticarcinogenic protective enzymes from broccoli: isolation and elucidation of structure. Proc Natl Acad Sci USA 1992; 89: 2399-2403.
10. Fahey J W, Zhang Y, Talalay P. Broccoli sprouts: an exceptionally rich source of inducers of enzymes that protect against chemical carcinogens. Proc Natl Acad Sci USA 1997; 94: 10367-10372.
11. Zhang Y. Allyl isothiocyanate as a cancer chemopreventive phytochemical. Mol Nutr Food Res 2010; 54: 127-35.
12. Bhattacharya A, Tang L, Li Y, et al. Inhibition of Bladder Cancer Development by Allyl Isothiocyanate. Carcinogenesis 2010; 31: 281-86.
13. Zhang Y, Munday R, Jobson H E, Munday C M, Lister C, Wilson P, Fahey J W, Mhawech-Fauceglia P. Induction of GST and NQO1 in cultured bladder cells and in the urinary bladders of rats by an extract of broccoli (*brassica oleracea* italica) sprouts. J Agric Food Chem 2006; 54: 9370-9376.
14. Zhang Y. Cancer-preventive isothiocyanates: measurement of human exposure and mechanism of action. Mutation Res 2004; 555: 173-190.
15. Johansson N L, Pavia C S, Chiao J W. Growth inhibition of a spectrum of bacterial and fungal pathogens by sulforaphane, an isothiocyanate product found ing broccoli and other cruciferous vegetables. Planta Med 2008; 74: 747-750.

16. Zhang Y, Tang L. Discovery and development of sulforaphane as a cancer chemopreventive phytochemical. Acta Pharmacol Sin 2007; 28: 1343-1354.
17. Jo H, Loison F, Hattori H, Silberstein L E, Yu H, Luo H R. Natural product Celastrol destabilizes tubulin heterodimer and facilitates mitotic cell death triggered by microtubule-targeting anti-cancer drugs. PLoS One 2010; 5: e10318.
18. Munday R, Mhawech-Fauceglia P, Munday C M, et al. Inhibition of urinary bladder carcinogenesis by broccoli sprouts. Cancer Res 2008; 68: 1593-600.

We claim:

1. A composition comprising a mixture of broccoli seed and mustard seed, wherein the broccoli seed has been subjected to baking and a pressurized heat treatment before being mixed with the mustard seed, wherein the broccoli seed was baked at a temperature of at least 200 degrees Fahrenheit for at least 60 minutes before being mixed with the mustard seed, and wherein the broccoli seed comprises heat inactivated epithiospecifier protein (ESP), and wherein the mustard seed has not been subjected to a heat or pressurized treatment, and wherein the broccoli seed is present in an amount effective to inhibit growth of bladder cancer an individual in need of thereof.

2. The composition of claim 1, wherein the pressurized heat treatment comprises a pressurized steam treatment at a temperature of at least 200 degrees Fahrenheit at a pressure of at least 10 pounds/square inch (p.s.i.) for at least 5 minutes.

3. The composition of claim 1, wherein the broccoli seed comprises at least 90 micromoles/gram glucoraphanin.

4. The composition of claim 1, wherein the mustard seed comprises at least 90 micromoles/gram sinigrin.

5. The composition of claim 1, wherein the mixture of the brocolli seed and the mustard seed is powdered.

6. The composition of claim 1, further comprising horseradish meal or powder, wasabi powder, or a combination thereof.

* * * * *